United States Patent
Bier et al.

(10) Patent No.: US 11,352,654 B2
(45) Date of Patent: Jun. 7, 2022

(54) COMPOSITION AND METHODS FOR PROCESSING A SPUTUM SAMPLE

(71) Applicant: Roche Molecular Systems, Inc., Pleasanton, CA (US)

(72) Inventors: Carolin Bier, Oberaegeri (CH); Stefan Lange, Mettmenstetten (CH); Pirmin Hans Loetscher, Hochdorf (CH)

(73) Assignee: Roche Molecular Systems, Inc., Pleasanton, CA (US)

(*) Notice: Subject to any disclaimer, the term of this patent is extended or adjusted under 35 U.S.C. 154(b) by 63 days.

(21) Appl. No.: 16/223,781

(22) Filed: Dec. 18, 2018

(65) Prior Publication Data
US 2019/0194716 A1 Jun. 27, 2019

(30) Foreign Application Priority Data
Dec. 22, 2017 (EP) .................................... 17210184

(51) Int. Cl.
*A01N 31/02* (2006.01)
*A01N 31/08* (2006.01)
*C12Q 1/04* (2006.01)
*G01N 1/28* (2006.01)

(52) U.S. Cl.
CPC ............. *C12Q 1/04* (2013.01); *A01N 31/02* (2013.01); *A01N 31/08* (2013.01); *G01N 1/28* (2013.01)

(58) Field of Classification Search
None
See application file for complete search history.

(56) References Cited

U.S. PATENT DOCUMENTS

| 8,652,782 | B2 | 2/2014 | Fischer et al. | |
|---|---|---|---|---|
| 2004/0141798 | A1* | 7/2004 | Garabedian, Jr. | A47L 13/22 401/279 |
| 2011/0281754 | A1* | 11/2011 | Fischer | C12Q 1/6806 506/9 |
| 2016/0024561 | A1* | 1/2016 | Tang | C12Q 1/689 435/6.12 |
| 2019/0082684 | A1* | 3/2019 | Leslie | A01N 25/30 |

FOREIGN PATENT DOCUMENTS

| CN | 103884549 A | * | 6/2014 |
|---|---|---|---|
| WO | 2013148346 A1 | | 10/2013 |

OTHER PUBLICATIONS

Saraswathy et al., "Chemical Composition and Antibacterial Activity of Essential Oil of Thymus Vulgaris Linn. Whole Plant", Asian Journal of Pharmacy and Life Science, vol. 3, pp. 16-21 (Year: 2013).*
Wexford Innovations, Wexford Innovations website, "Ready to Use Thymo-Cide", https://www.wexfordinnovations.com/products/ready-to-use-thymo-cide/; accessed Oct. 6, 2020 (Year: 2019).*
US EPA "List B: EPA's Registered Tuberculocide Products Effective Against Mycobacterium tuberculosis", Apr. 1, 2014 (Apr. 1, 2014), pp. 1-14,XP055216102,U.S.A. Retrieved from the Internet: URL:http://www.epa.gov/oppad001/listbtuberculocide. pdf[retrieved on Sep. 25, 2015]*p. 10 *.
European search report dated Mar. 27, 2018 issued in corresponding EP application No. 172101842-1110 pp. 1-10.
Sergio Andrade-Ochoa et al: "Quantitative structure-activity relationship of molecules constituent of different essential oils with antimycobacterial activity against Mycobacterium tuberculosis and Mycobacterium bovis", BMC Complementary and Alternativemedicine, vol. 15, No. 1, Sep. 23, 2015 (Sep. 23, 2015),XP055459747, DOI: 10.1186/s12906-015-0858-2 * the whole document *.
Veronica Allen et al: Sputum Processing Prior to Mycobacterium tuberculosis Detection by Culture or Nucleic Acid Amplification Testing: A Narrative Review, Journal of Microbiology and Biotechnology, Mar. 29, 2016 (Mar. 29, 2016), pp. 96-108,XP055461020.
Yajko et al: "Quantitative culture of Mycobacterium tuberculosis from clinical sputum specimens and dilution endpoint ofits detection by the Amplicor PCR assay.", Journal of Clinical Microbiology, vol. 33, No. 7, Jul. 1, 1995 (Jul. 1, 1995),pp. 1944-1947, XP055009136, ISSN: 0095-1137* p. 1944, right column; p. 1946, right column *.

* cited by examiner

*Primary Examiner* — Michelle F. Paguio Frising
(74) *Attorney, Agent, or Firm* — David J. Chang

(57) ABSTRACT

The present disclosure relates to a composition and its use for treating a sputum sample suspected to contain mycobacteria. The composition comprises thymol, a linear or branched alcohol, a chaotropic agent, a reducing agent, a detergent, and a buffer, and has a pH value between 8.5 and 10. Also disclosed is a method for treating a sputum sample suspected to contain mycobacteria.

5 Claims, No Drawings

COMPOSITION AND METHODS FOR PROCESSING A SPUTUM SAMPLE

CROSS REFERENCE TO RELATED APPLICATIONS

This application claims the benefit of priority to European Application No. EP 17210184.2, filed on Dec. 22, 2017, the content of which is incorporated by reference herein in its entirety.

FIELD OF THE INVENTION

The present invention belongs to the field of processing biological samples, such as a sample containing bacteria. Within this field, it concerns a composition and a method for treating a sputum sample.

BACKGROUND OF THE INVENTION

The isolation of biological materials such as nucleic acids or proteins from complex biological mixtures such as e.g. clinical samples has been of considerable significance especially for diagnostic purposes.

Examples for diagnostic applications of biological sample preparation comprise preparation and subsequent detection of viruses or bacterial targets. Especially in a clinical environment, such techniques often require the handling of highly pathogenic material such as living bacterial cells that may pose a significant risk of infection for the person conducting the preparation. Therefore, it may be important to inactivate the respective pathogens as a safety measure. In many instances, such inactivation may be achieved by a typical preparation step in which viral particles or bacterial cells are lysed such that the respective contents are released, before further measures for the enrichment of the analyte in question may be applied. Standard lysis procedures for most of the common viral particles and bacterial cells are well-established and known to the person of skill in the art.

However, certain pathogens require a more rigorous treatment for a successful inactivation, including species of the *Mycobacterium tuberculosis* complex (MTBC), in the following also referred to as "mycobacteria". These bacteria are enveloped by a relatively thick and complex cell wall that exhibits a considerably higher robustness than their counterparts found in most other clinically relevant bacteria.

An additional challenge is provided by the samples usually required for the diagnosis of mycobacteria. MTBC species are typically detected in sputum, which is per se a demanding sample matrix requiring more complex treatment than many other clinical sample types such as, for instance, blood plasma. Raw sputum tends to be a highly viscous matter often requiring liquefying before it can be processed.

Pertinent approaches applied in the art include, for example, U.S. Pat. No. 862,782, teaching the use of compositions contain various surfactants, chaotropes, buffers, detergents, and other components. Practical use has shown that inactivation of mycobacteria may not always be optimal, as described herein below.

The present disclosure describes an improved approach for processing sputum samples suspected to contain mycobacteria.

SUMMARY OF THE INVENTION

In a first aspect, a composition is disclosed for treating a sputum sample suspected to contain mycobacteria. The composition provides for liquefying of the sputum which is otherwise often difficult to handle, particularly with common liquid handling systems such as pipettors. The composition further allows for the inactivation of the mycobacteria if present in the sample. Its active ingredients include thymol, a linear or branched alcohol, a chaotropic agent, a reducing agent, a detergent, and a buffer. The pH value of the composition is between 8.5 and 10.

Another aspect disclosed herein is a method for treating a sputum sample suspected to contain mycobacteria. In brief, the sputum is contacted and mixed with a composition as described herein, then incubated under suitable conditions for liquefying the sputum and inactivation of the mycobacteria.

A further aspect disclosed herein is the use of a composition as described herein for treating a sputum sample suspected to contain mycobacteria.

DETAILED DESCRIPTION OF THE INVENTION

A first aspect described herein is a composition treating a sputum sample suspected to contain mycobacteria, the composition comprising the following components:
thymol
a linear or branched alcohol
a chaotropic agent
a reducing agent
a detergent
a buffer,
wherein the composition has a pH value between 8.5 and 10.

Tuberculosis (TB) is a bacterial infection caused by species of the above-described *Mycobacterium tuberculosis* complex (MTBC). TB remains a major global health problem, ranking among the top 10 causes of death, and the emergence of drug-resistant strains of *M. tuberculosis* is a growing threat worldwide. The diagnosis of TB is confirmed by recovery of *M. tuberculosis* bacilli from clinical samples—for pulmonary tuberculosis from respiratory samples such as sputum. As mentioned above, those samples constitute a major challenge in terms of biosafety, further processing in automated workflows due to high sample viscosity and compatibility for diagnostic testing because of high loads of sample inherent interfering substances. Currently, there is no commercial reagent available that adequately balances all of above mentioned challenges. The composition described herein allows to effectively inactivate *Mycobacterium tuberculosis* complex bacilli up to 5E+07 CFU/mL, liquefies respiratory samples and is compatible with automated sample extraction workflows that can be used in molecular diagnosis with a reagent stability of equal to or greater than 18 months.

"Sputum" is the thick mucus or phlegm that is expelled from the lower respiratory tract (bronchi and lungs) through coughing; it is not saliva or spit. Typically, sputum includes a considerable amount of the glycoprotein sputum. In the sample collection process, the sample is retrieved from the lower airways and not from the upper respiratory tract. An unprocessed sample of sputum is also referred to herein as "raw sputum". In some embodiments described herein, the sputum sample is a raw sputum sample. Alternatively, the sputum collected from a patient may be diluted with, for example, a common buffer such as Tris, citrate, or the like. Such buffers do typically not substantially contribute to altering the difficult handling properties of a sputum sample, i.e. the sputum may still remain a viscous and mostly immiscible matter within the diluent. In such cases, addition of a composition such as the composition disclosed herein will be required in order to make the sputum amenable to further processing by conventional liquid handling devices and methods.

The presently disclosed composition, in some embodiments an aqueous solution, comprises various chemical compounds with distinct functional activities allowing for liquefaction of a patient sample (digestion of the sample matrix by reduction of disulfide bonds of mucin-rich respiratory samples by a reducing agent) and inactivation of *M. tuberculosis* bacilli by bacterial cell wall damage, protein denaturation and other mechanisms by a detergent, a chaotropic agent, a linear or branched alcohol, and thymol as a naturally occurring biocide with strong antimicrobial attributes. Integrity of clinically relevant biological material, especially the mycobacterial nucleic acids, is substantially maintained such that it can be subjected to downstream analysis. The pH of the reagent has a value of between 8.5 and 10 such that it balances between nucleic acid stability and reduced interfering characteristics of sample inherent substances such as mucin proteins by pH-dependent conformational changes.

"Thymol" (2-isopropyl-5-methylphenol) is a natural monoterpene phenol derivative of cymene, found in oil of thyme, and extracted from Thymus vulgaris (common thyme) and various other kinds of plants as a white crystalline substance. It is only slightly soluble in water at neutral pH, but highly soluble in alcohols and other organic solvents. It is also soluble in strongly alkaline aqueous solutions due to deprotonation of the phenol moiety.

Thymol may be present in the composition described herein in a range of different concentrations. In some embodiments, it is applied in a concentration (w/v) from 0.75%, 1%, or 1.5% to 2%, 3.5%, or 5%. In a more specific embodiment, thymol is present in a concentration of about 1% (w/v). As the inventors have shown, thymol has proven very effective as a part of the composition disclosed herein in the context of inactivating members of the MTBC.

The "linear or branched alcohol" also contributes to inactivation of mycobacteria that may be present in the sputum sample, especially in combination with thymol. Among linear or branched alcohols useful in the context described herein are, for example, short-chain alkanols with up to 10 carbon atoms chain length. It may be a primary, secondary, or tertiary alcohol. In specific embodiments, it may be a secondary alcohol. In more specific embodiments, the alkanol chain has from 1 to 5 carbon atoms, for example, methanol, ethanol, propanol, butanol, or pentanol, or any of their branched derivatives. In even more specific embodiments, the alkanol is selected from the group of propanol and its derivatives. In a more specific embodiment, the alkanol is isopropanol. Isopropanol (also isopropyl alcohol) is a compound with the chemical formula $C_3H_8O$. It is a colorless, flammable chemical compound with a strong odor. As an isopropyl group linked to a hydroxyl group, it is the simplest example of a secondary alcohol, where the 1 carbon atom carrying the hydroxyl group is attached to two other carbon atoms.

The linear or branched alcohol may be present in the composition described herein in concentrations ranging from 20%, 30%, or 45% to 50%, 60%, 70%, or 80% (v/v). In some embodiments, the concentration is from 45% to 60%. In more specific embodiments, the concentration is 60%.

"Chaotropic agents" are substances that generally disturb the ordered structure of water molecules in solution and non-covalent binding forces in and between molecules. They can make several contributions to the procedure of sample preparation. Besides, chaotropic agents contribute to the disruption of biological membranes, such as plasma membranes or the membranes of cell organelles if present. Non-limiting examples of chaotropic agents are guanidinium salts like guanidinium thiocyanate, guanidinium hydrochloride, guanidinium chloride or guanidinium isothiocyanate, urea, perchlorates such as potassium perchlorate, other thiocyanates or potassium iodide or sodium iodide. In some embodiments described herein, the chaotropic agent is a guanidinium salt. In more specific embodiments, the chaotropic agent is guanidinium thiocyanate (GuSCN).

The chaotropic agent may be present in the composition described herein in a concentration range from 0.5 M, 1 M, or 1.2 M to 2 M, 3.5 M, or 5 M. In more specific embodiments, the concentration may range from 1.2 M to 2 M. In a yet more specific embodiment, the concentration may be about 1.6 M.

The "reducing agent", as used herein, can also contribute to the denaturation of undesired components. In particular, reducing agents, as widely known in the art, cleave inter- and intramolecular disulfide bonds, which are especially important for the tertiary structure of many proteins. In the context described herein, the disulfide bonds of the high molecular weight mucin glycoproteins, predominant components of sputum, are broken such that the overall viscosity of the sample is decreased. Useful in the context of the invention are reducing agents such as e.g. dithiothreitol (DTT), but other reducing agents known in the art such as e.g. 2-mercaptoethanol can also be employed. In some embodiments, the reducing agent is TCEP (tris(2-carboxyethyl)phosphine). Compared to the other agents mentioned above, TCEP has the advantages of being odorless, a more powerful reducing agent, an irreversible reducing agent (in the sense that TCEP does not regenerate—the end product of TCEP-mediated disulfide cleavage is in fact two free thiols/cysteines), more hydrophilic, and more resistant to oxidation in air. It also does not reduce metals used in immobilized metal affinity chromatography. TCEP may be used in the composition as described herein, for instance, as a hydrochloride.

The reducing agent may be present in the composition described herein in concentrations ranging from 1 mM, 2.5 mM, 5 mM, or 10 mM to 75 mM, 100 mM 250 mM, or 500 mM. In more specific embodiments, the range is from 5 mM to 75 mM. In a yet more specific embodiment, the concentration is about 50 mM.

The "detergent" used as a component of the composition described herein also contributes to effects such as denaturation of plasma membrane or cell wall components, denaturation of certain proteins, and the like. Detergents useful in the context described herein include ionic detergents such as sodium dodecyl sulfate (SDS), lithium dodecyl sulfate, sodium taurodeoxycholate, sodium taurocholate, sodium glycocholate, sodium deoxycholate, sodium cholate, sodium alkylbenzene sulfonate, N-lauroyl sarcosine, or any combination thereof. In some embodiments described herein, the detergent is a non-ionic detergent, for example, Tween-20, Nonidet P40, CHAPs, a member of the Brij series, or Triton X-100. In more specific embodiments, the detergent is Tween-20. Non-ionic detergents have a hydrophilic head group that is uncharged and are preferred for their ability to break lipid-lipid and lipid-protein interactions. They have limited ability to break protein-protein interactions and are often referred to as non-denaturing detergents and are used to isolate biologically active membrane proteins.

The detergent may be present in the composition described herein in concentrations ranging from 0.01%, 0.05%, or 0.1%, to 0.5%, 1%, 2.5%, 5%, or 10% (w/v or v/v). In some embodiments, the concentration ranges from 0.1% to 1%. In more specific embodiments, the concentration is about 0.4%.

The "buffer" mainly provides for establishing and maintaining a certain pH value or range. Suitable buffers in the context described herein include, for instance, tris(hydroxymethyl)aminomethane (Tris), citrate, 2-(N-morpholino)ethanesulfonic acid, N,N-Bis(2-hydroxyethyl)-2-aminoethanesulfonic acid, 1,3-bis(tris(hydroxymethyl)methylamino)propane, 4-(2-hydroxyethyl)-1-piperazineethanesulfonic acid (HEPES), 3-(N-morpholino)propanesulfonic acid (MOPS), piperazine-N,N'-bis(2-ethanesulfonic acid) (PIPES), bicarbonate, phosphate, or any combination thereof. In more specific embodiments, the buffer is Tris (also known as Trizma, Trizma base, THAM, or other synonyms).

The buffer may be present in the composition described herein in a concentration ranging from 1 mM, 10 mM, 100 mM, or 250 mM, to 750 mM, 1 M, 2 M, or 5 M. In more specific embodiments, the concentration range may be from 375 mM to 635 mM. In yet more specific embodiments, the concentration is about 500 mM.

The pH value of the composition disclosed herein may range from 8.5 to 10. In some embodiments, it may be about 8.5, 9, 9.5 or 10. In more specific embodiments, it ranges from 8.7 to 9.3. In yet more specific embodiments, it is about 9.

Measures and reagents are well known in the art to adjust the pH value. As the composition described herein has an alkaline pH, bases such as, for instance, alkaline bases are among the suitable substances. In some embodiments, an alkali hydroxide is used as a base. In more specific embodiments, sodium hydroxide is used. The concentration of such a base in the composition disclosed herein may range from 1 mM, 10 mM or 100 mM to 150 mM, 250 mM, or 500 mM. In more specific embodiments, the concentration may be about 100 mM, or about 112 mM.

In a specific embodiment, the composition described herein comprises the following components:
Thymol 0.75%-5%
Isopropanol 45-60% (v/v)
GuSCN 1.2 M-2 M
TCEP 5 mM-75 mM
Tween-20 0.4%
Trizma 375 mM-625 mM.

Also described herein is a method for treating a sputum sample suspected to contain mycobacteria, the method comprising the following steps:
a) contacting a sputum sample with the composition disclosed herein
b) mixing the resulting fluid
c) incubating the mixture for a period of time and under conditions sufficient for liquefying the sample and inactivating mycobacteria if present in the sample.

The embodiments of the composition disclosed herein also apply to the method described herein.

The benefits of using the composition disclosed herein for treating a sputum sample, especially in terms of sputum liquefaction and mycobacteria inactivation, are described elsewhere in the present disclosure.

The method described herein is especially useful in cases where the sputum sample is raw sputum, as detailed in the context of the composition disclosed herein. By means of the method and composition described herein, even raw sputum may be successfully processed without prior dilution. However, in case such dilution is performed, the method described herein is also applicable to diluted or otherwise pretreated sputum.

Contacting the sputum sample with the composition disclosed herein and mixing it therewith may be performed within the same step. For instance, a vessel containing the sputum may be placed on a shaker such that agitation of the sample may readily be performed when the composition is added. Alternatively, sputum may be added to a vessel containing the composition while said vessel is vortexed or otherwise agitated. Such a workflow may streamline the method by saving time and potentially space. Hence, in some embodiments of the method disclosed herein, step a) and step b) are performed at the same time.

However, in other embodiments of the method, the sputum sample and the composition may be contacted with each other first, and then transferred to, for instance, a shaker, a stirrer, or the like, and mixed subsequently. Therefore, in some embodiments of the method described herein, step a) and step b) are temporally and/or locally separated.

Means for performing the mixing are known to the person of skill in the art. As mentioned above, shakers or vortexes are among the most common devices for this purpose. In some embodiments, the mixture is shaken or vortexed for between 5 and 60 seconds. In some embodiments, this period of time is about 30 seconds.

Incubation of the sample/composition mixture can be conducted under a variety of conditions and for different amounts of time.

In some embodiments, incubation in step c) is carried out essentially at room temperature, abolishing the need for thermostatic equipment. Room temperature is usually defined in the art as a range of 20° C. to 25° C. In some embodiments, the incubation temperature is about 25° C.

Also in some embodiments, the period of time for the incubation in step c) is at least 30 min. In some embodiments, it is between 30 and 90 min. In more specific embodiments, it is about 50 min, in other embodiments about 60 min.

The incubation may be combined or complemented with additional measures, such as sonication. The application of ultrasound to the mixture can contribute to both effects mentioned above, meaning liquefaction of the sputum sample and inactivation of the mycobacteria if present in the sample. Suitable sonicators are commercially available and known to the person skilled in the art. They may be conventional multi-purpose sonicators or tailor-made for the purpose described herein.

Hence, in some embodiments of the method disclosed herein, step c) involves sonication of the mixture, either during or subsequent to the incubation.

In some embodiments, the method described herein further comprises after step c) one or more of the following steps:
d) isolating a biological target material from the inactivated mycobacteria if present in the sample
e) analyzing the biological target material.

In the context of the present disclosure, the terms "isolation", "purification" or "extraction" of a biological target material relate to the following: Before biological target materials like, for instance, nucleic acids may be analyzed in a diagnostic assay by amplification or the like, they typically have to be purified, isolated or extracted from biological samples containing complex mixtures of different components. In the context described herein, the mycobacteria, if present in the sputum sample, contain a variety of different biomolecules, and in many cases only a subgroup of these molecules are of interest for a given type of analysis. For instance, nucleic acids to be analyzed by PCR in a downstream process may need to be separated from the other biomolecules present in the mixture subjected to step d) of the method disclosed herein. Suitable methods for isolation are known to the person skilled in the art.

Typically, one of the first steps comprises releasing the contents of cells or viral particles, for example, by using enzymes and/or chemical reagents. This process is commonly referred to as lysis. For enrichment of the analyte in question in the lysate, one useful procedure for binding nucleic acids entails the selective binding of nucleic acids to glass or silica surfaces of binding particles such as magnetic particles in chaotropic salt solutions and separating the nucleic acids from contaminants such as agarose, proteins or cell debris. The composition used herein may be especially useful when nucleic acids are bound to glass surfaces, as the composition already contains a chaotropic agent which is usually necessary for such binding.

Downstream analysis of the biological target material, as performed in step e) of the method disclosed herein, may include Polymerase Chain Reaction (PCR) or sequencing of nucleic acids, or antibody-mediated assays for proteins such as ELIZA, or the like. In some embodiments of the method described herein, the analysis comprises qualitative and/or quantitative detection of nucleic acids by amplification. In some embodiments, the amplification technique is PCR. Other amplification techniques, such as isothermal amplification (LAMP, TMA, and the like), LCR, etc. may be applied for analyzing a target nucleic acid.

In accordance with the composition and the method using it as described herein, another aspect of the present disclosure is the use of the composition described herein for treating a sputum sample suspected to contain mycobacteria. If safe handling and using liquid handling devices are desired, the use is for liquefying a sputum sample and inactivating mycobacteria if present in the sample.

The embodiments of the composition and the method disclosed herein also apply to the use described herein.

EXEMPLARY EMBODIMENTS

The following Examples are meant to illustrate specific embodiments of the composition, method and use disclosed herein, while they are not limiting.

Example 1

Liquid Handling

Particularly raw sputum, but often also diluted sputum, are matrices difficult to handle and not easily pipettable.

However, upon addition of the composition disclosed herein resulting in a 1:2 ratio, the sputum gets digested and the sample can be easily pipetted afterwards.

In this example, the composition was as follows: 1.6 M GuSCN, 0.4% Tween-20, 50 mM Tris(2-carboxyethyl)phosphine (TCEP) HCl, 500 mM Trizma Base (Tris), 112 mM NaOH, 60% 2-Isopropanol, 1% Thymol, pH 9.

Example 2

Inactivation of Two Different MTB Strains at Various Concentration Levels (2E+06 to 5E+07 CFU/mL) was Demonstrated at Three Different Testing Sites Experimental Setup:

Two different quantified MTB cultures (wildtype MTB and the laboratory strain H37v) were diluted to the intended target concentrations of 5E+07 CFU/mL, 1E+07 CFU/mL and 2E+06 CFU/mL. Aliquots of 0.5 mL of the cultures were mixed with 1 mL of the composition described herein (1.6M GuSCN, 0.4% Tween-20, 50 mM Tris(2-carboxyethyl)phosphine (TCEP) HCl, 500 mM Trizma Base (Tris), 112 mM NaOH, 60% 2-Isopropanol, 1% Thymol, pH 9). After an incubation time of 60 minutes at room temperature, the solution was centrifuged at 3000 g for 15 minutes, the supernatant was discarded and the pellet washed 2 times with DPBS (Dulbecco's phosphate-buffered saline), before it was suspended in 0.5 mL DPBS. For cultivation in the commercially available MGIT system (Beckton Dickinson (BD)), the solution was transferred into a MGIT tube together with 0.8 mL of the BD growth media in order to monitor growth. For the solid cultures, the solution was distributed on Löwenstein-Jensen plates stored in an incubator. For the MGIT system, growth is detected based on oxygen reduction, growth is detected on solid cultures by colony formation.

This study was conducted with two unique batches of the composition described herein, untreated samples for each concentration level were included as growth controls:

Multiple replicates were treated with either batch 1 or batch 2 of the composition disclosed herein at T0, after incubation for the intended time period and temperature, cells were washed with PBS (phosphate-buffered saline) and growth was initiated either according to the procedures used for the MGIT system or by established procedures on solid media types As growth controls, two replicates were treated with PBS only to mimic the procedure A result overview is given in the Table 1.

TABLE 1

Time point of growth detection after treatment

| | | Concentration MTB [cells/mL] | | | | | | | | |
|---|---|---|---|---|---|---|---|---|---|---|
| | | 2.0E+06 | | | 1.0E+07 | | | 5.0E+07 | | |
| | | Composition batch | | | | | | | | |
| | | 1 | 2 | n/a* | 1 | 2 | n/a* | 1 | 2 | n/a* |
| MTB | Site 1 | no growth | no growth | 18-20 days | no growth | no growth | 15-16 days | no growth | no growth | 12-14 days |
| | Site 2 | no growth | no growth | 16 days | no growth | no growth | 11 days | no growth | no growth | 9-10 days |
| | Site 3 | no growth | no growth | growth detected** | no growth | no growth | growth detected** | no growth | no growth | growth detected** |
| MTB H37 | Site 1 | no growth | no growth | 18-21 days | no growth | no growth | 12-13 days | no growth | no growth | 11-12 days |
| | Site 2 | no growth | no growth | 14 days | no growth | no growth | 14-18 days | no growth | no growth | 10-11 days |
| | Site 3 | no growth | no growth | growth detected** | no growth | no growth | growth detected** | no growth | no growth | growth detected** |

*growth control
**solid media was used (manual check), read out is not as precise as with the automated detection by MGIT Over the time course of the study (52 days), no growth was detected in the replicates treated with the composition disclosed herein, while all growth controls had detectable growth independent of the concentration.

Example 3

Effect of pH Value on Liquefaction

Mucin is a glycoprotein family abundant in sputum samples and known to be inhibitory for, as an example, automated nucleic acid extraction. These inhibitory effects can be influenced by the protein conformation which is different depending on the pH value. In order to determine the optimal pH variants of the composition described herein, different pH levels were tested: pH 7.5, 8.0, 8.5, 9.0, 9.5 and 10.0.

Experimental Setup:

In order to test extraction and amplification of MTB complex DNA under inhibitory conditions, 500 CFU/mL of *Mycobacterium bovis* Bacillus Calmette-Guérin (BCG) were spiked into a matrix containing 1% mucin and treated with one of the different pH variants of the composition described herein. Performance was evaluated by testing 5 replicates on the Cobas® 6800/8800 systems (Roche Diagnostics) with the Cobas® MTB test (Roche Diagnostics) according to the manufacturer's instructions.

Results are displayed in Table 2:

|      | Channel 2 Positive | | | | Channel 5 Positive | | | |
|------|------|------|------|------|------|------|------|------|
|      | Ct [2] | | RFI [2] | | Ct [5] | | RFI [5] | |
| pH   | Mean | SD | Mean | SD | Mean | SD | Mean | SD |
| 7.5  | 35.3 | 0.29 | 2.2 | 0.11 | 39.2 | 1.10 | 8.7 | 0.41 |
| 8.0  | 35.0 | 0.47 | 2.9 | 0.30 | 38.2 | 0.42 | 9.2 | 0.33 |
| 8.5  | 32.0 | 0.26 | 7.6 | 0.87 | 31.4 | 0.24 | 9.4 | 0.05 |
| 9.0  | 31.7 | 0.15 | 9.2 | 0.21 | 30.6 | 0.09 | 9.2 | 0.05 |
| 9.5  | 32.0 | 0.22 | 8.9 | 0.23 | 30.8 | 0.19 | 9.2 | 0.05 |
| 10.0 | 31.5 | 0.17 | 9.4 | 0.20 | 30.6 | 0.12 | 9.3 | 0.06 |

The performance of any solution with a pH≥8.5 and ≤10.0 is suitable, as indicated by comparable Cts and RFIs for the target channel, as well as the channel of the internal control.

Example 4

Optimal Concentration of Components

The tolerance ranges of concentrations of individual components of the composition disclosed herein were determined. In order to determine those ranges, different variants of the solution were generated, which were tested against two reference batches.

a) Four components were tested due to potentially impacting the stability and detection of nucleic acids, as well as the level of interference caused by proteins present in the matrix: guanidinium thiocyanate (GuSCN), Trizma Base (Tris), NaOH, and the resulting pH value. In consequence, the following compositions were tested:

| Component | Reference conc | Solution 1 | Solution 2 | Solution 3 | Solution 4 |
|---|---|---|---|---|---|
| GuSCN | 1.6M | 1.2M | 1.2M | 2.0M | 2.0M |
| Tween-20 | | | 0.4% (w/v) | | |
| TCEP HCl | | | 50 mM | | |
| Isopropanol | | | 60% (v/v) | | |
| NaOH | 112 mM | | Titrated for pH | | |
| Trizma Base | 500 mM | 375 mM | 625 mM | 375 mM | 625 mM |
| Thymol | | | 0% (w/v) | | |
| pH | 9.0 | 8.7 | 9.3 | 8.7 | 9.3 |

Experimental Setup:

A clinical sediment panel low positive for MTB was mixed 1:9 with one of the compositions described herein (denoted as "solutions", see below) or one of the two reference solutions. The respective diluted sample was vortexed for 30 sec, incubated for 50 minutes at room temperature, sonicated and centrifuged for 1 min at 3000 g, before the sample was loaded onto the Cobas® 6800/8800 system.

For all conditions tested all tested replicates were positive, neither RFI nor Ct had shown any significant difference, therefore the performance was considered equivalent.

b) Three components were tested due to potentially impacting inactivation properties of the composition described herein: guanidinium thiocyanate (GuSCN), isopropanol, and thymol. The following compositions were tested:

| Component | Reference conc | Solution 5 | Solution 6 | Solution 7 | Solution 8 | Solution 9 |
|---|---|---|---|---|---|---|
| GuSCN | 1.6M | 1.2M | 1.6M | 1.6M | 1.2M | 1.6M |
| Tween-20 | | | 0.4% (w/v) | | | |
| TCEP HCl | | | 50 mM | | | |
| Isopropanol | 60% (v/v) | 60% (v/v) | 45% (v/v) | 60% (v/v) | 45% (v/v) | 60% (v/v) |
| NaOH | | | 112 mM | | | |
| Trizma Base | | | 500 mM | | | |
| Thymol | 1% (w/v) | 1% (w/v) | 1% (w/v) | 0.75% (w/v) | 0.75% (w/v) | 5% (w/v) |
| pH | | | 9.0 | | | |

Experimental Setup:

Two different quantified MTB cultures (wildtype MTB and the laboratory strain H37v) were diluted to the intended target concentrations of 5E+07 CFU/mL and 2E+06 CFU/mL. Aliquots of 0.5 mL of the cultures were mixed with either of the solutions or the reference solution. After an incubation time of 50 minutes at room temperature, the mixture was centrifuged at 3000 g for 15 minutes, the supernatant was discarded and the pellet washed 2 times with DPBS, before it was suspended in 0.5 mL DPBS. For cultivation in the MGIT system (BD), the solution was transferred into a MGIT tube together with 0.8 mL of the BD growth media in order to monitor growth. This study was conducted with two unique batches of the composition described herein and 5 of its variants, untreated samples for each concentration level were included as growth controls:

- Multiple replicates were treated with either batch of the composition at T0. After incubation for the intended time period and temperature, cells were washed with PBS and growth was initiated either according to the procedures used for the BD MGIT system or by established procedures on solid media types.
- As growth controls, two replicates were treated with PBS only to mimic the procedure.

A result overview is given in Table 3.

TABLE 3

| Time point of growth detection after treatment | | | | | | | |
|---|---|---|---|---|---|---|---|
| | Concentration MTB [cells/mL] | | | | | | |
| Strain | Reference conc | Solution 5 | Solution 6 | Solution 7 | Solution 8 | Solution 9 | n/a* |
| | 2.0E+06 | | | | | | |
| MTB | no growth | no growth | no growth | no growth | no growth | no growth | 17 days |
| MTB H37 | no growth | no growth | no growth | no growth | no growth | no growth | 6-13 days |
| | 5.0E+07 | | | | | | |
| MTB | no growth | no growth | no growth | no growth | no growth | no growth | 6 days |
| MTB H37 | no growth | no growth | no growth | no growth | no growth | no growth | 3 days |

*growth control

Over the time course of the study (52 days), no growth was detected in the MIS or MIS variants treated replicates, while all growth controls had detectable growth independent of the concentration, therefore inactivation potential is considered equal for all tested formulations.

c) TCEP, a reducing agent with major contribution to liquefying the sputum samples, was tested in seven additional solutions in which only the TCEP concentration was titrated:

0 mM TCEP
2.5 mm TCEP
5 mM TCEP
10 mM TCEP
20 mM TCEP
30 mM TCEP
40 mM TCEP
75 mM TCEP
100 mM TCEP

All other components of the composition described herein remained equal to the used reference (1.6 M GuSCN, 0.4% Tween-20, 50 mM Tris(2-carboxyethyl)phosphine (TCEP) HCl, 500 mM Trizma Base, 112 mM NaOH, 60% 2-Isopropanol, 1% Thymol, pH 9)

Experimental Setup:

A 12% mucin solution, used to simulate conditions found in raw sputum, was mixed with one of the different variants of the composition disclosed herein, vortexed for 30 sec and incubated for 50 min at room temperature. Liquefaction capacities were assessed after incubation. Already 5 mM TCEP were sufficient in order to show a good liquefaction of the sample.

The entire titration study demonstrated that the following concentration ranges of the used components led to good liquefaction:

GuSCN 1.2 M-2.0 M
Tween-20 0.4% (w/v)
TCEP HCl 5-75 mM
Isopropanol 45-60% (v/v)
NaOH 112 mM
Trizma Base 375-625 mM
Thymol 0.75-5%
pH 8.7-9.3

Example 5

Inactivation Comparison Against Existing Products was Performed Directly Against the Prime Store Solution Commercially Available by the Company LongHorn Experimental Setup:

Two different quantified MTB cultures (wildtype MTB and the laboratory strain H37v) were diluted to the intended target concentrations of 5E+07 CFU/mL and 2E+06 CFU/mL. Aliquots of 0.4 mL of the cultures were mixed with either 0.8 mL of the composition disclosed herein or the Prime store solution. After an incubation time of 50 minutes at room temperature, the solution was centrifuged at 3000 g for 15 minutes, the supernatant was discarded and the pellet washed 2 times with DPBS, before it was suspended in 0.5 mL DPBS. For cultivation in the MGIT system (BD), the solution was transferred into a MGIT tube together with 0.8 mL of the BD growth media in order to monitor growth. This study was conducted with two unique batches of the composition described herein, untreated samples for each concentration level were included as growth controls:

- Multiple replicates were treated with either the composition described herein or Prime Store at T0. After incubation for the intended time period and temperature, cells were washed with PBS and growth was initiated either according to the procedures used for the BD MGIT system or by established procedures on solid media types
- As growth controls, two replicates were treated with PBS only to mimic the procedure A result overview is given in Table 4.

TABLE 4

Time point of growth detection after treatment

| | Concentration MTB [cells/ mL] | | | | | |
|---|---|---|---|---|---|---|
| | 2.0E+06 | | | 5.0E+07 | | |
| Strain | Composition | Prime Store | n/a* | Composition | Prime Store | n/a* |
| MTB | no growth | 13-14 days | 17 days | no growth | 9-10 days | 6 days |
| MTB H37 | no growth | 11 days | 6-13 days | no growth | 7-8 days | 3 days |

*growth control

Over the time course of the study (52 days), no growth was detected in the replicates treated with the composition disclosed herein, while all growth controls and the Prime Store treated replicates had detectable growth independent of the concentration, therefore inactivation performance can be considered superior in comparison to existing products.

The invention claimed is:

1. A composition comprising an aqueous solution for liquefaction of a sputum sample suspected to contain mycobacteria and for inactivation of said mycobacteria, the composition comprising:
   a) thymol in a concentration from 0.75% to 5%;
   b) isopropanol;
   c) a chaotropic agent comprising guanidinium thiocyanate (GuSCN);
   d) a reducing agent in a concentration from 5 mM to 75 mM and selected from the group consisting of dithiothreitol (DTT), 2-mercaptoethanol, and TCEP (tris(2-carboxyethyl)phosphine);
   e) a non-ionic detergent in a concentration from 0.1% to 1% and selected from the group consisting of polyoxyethylene (20) sorbitan monolaurate (Tween® 20), octylphenoxypolyethoxyethanol (Nonidet® P40), 3-[(3-cholamidopropyl)dimethylammonio]-1-propanesulfonate (CHAPs), a member of the polyoxyethylene alkyl ethers (Brij®) series, and 2-[4-(2,4,4-trimethylpentan-2-yl)phenoxy]ethanol (Triton® X-100); and
   f) a buffer selected from the group consisting of tris(hydroxymethyl)aminomethane (Tris/Trizma®), 2-(N-morpholino)ethanesulfonic acid, N,N-Bis(2-hydroxyethyl)-2-aminoethanesulfonic acid, 1,3-bis(tris(hydroxymethyl)methylamino)propane, 4-(2-hydroxyethyl)-1-piperazineethanesulfonic acid (HEPES), 3-(N-morpholino)propanesulfonic acid (MOPS), and piperazine-N,N'-bis(2-ethanesulfonic acid) (PIPES);
   wherein the composition has a pH value between 8.5 and 10.

2. The composition of claim 1, wherein the reducing agent is TCEP (tris(2-carboxyethyl)phosphine).

3. The composition of claim 1, wherein the non-ionic detergent is Tween® 20.

4. The composition of claim 1, wherein the buffer is tris(hydroxymethyl)aminomethane (Tris/Trizma®).

5. The composition of claim 1, comprising the following components:
Thymol 0.75%-5%;
Isopropanol 45-60% (v/v);
GuSCN 1.2 M 2 M;
TCEP 5 mM 75 mM;
Tween® 20 0.4%; and
Tris/Trizma® 375 mM-625 mM.

* * * * *